(12) United States Patent
Jeong et al.

(10) Patent No.: US 12,226,523 B2
(45) Date of Patent: Feb. 18, 2025

(54) METHOD FOR PREPARING SELF-ASSEMBLED NANOPARTICLE RELEASING SOLUBLE MICRONEEDLE STRUCTURE

(71) Applicant: RESEARCH & BUSINESS FOUNDATION SUNGKYUNKWAN UNIVERSITY, Suwon-si (KR)

(72) Inventors: Ji Hoon Jeong, Yongin-si (KR); Nak Won Kim, Gwangmyeong-si (KR)

(73) Assignee: RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 0 days.

(21) Appl. No.: 18/511,120

(22) Filed: Nov. 16, 2023

(65) Prior Publication Data

US 2024/0156721 A1 May 16, 2024

Related U.S. Application Data

(62) Division of application No. 16/082,705, filed as application No. PCT/KR2017/002425 on Mar. 7, 2017, now abandoned.

(30) Foreign Application Priority Data

Mar. 7, 2016 (KR) .................. 10-2016-0027240
Mar. 2, 2017 (KR) .................. 10-2017-0027220

(51) Int. Cl.

| | | |
|---|---|---|
| A61K 9/00 | (2006.01) | |
| A61K 9/51 | (2006.01) | |
| A61K 31/437 | (2006.01) | |
| A61K 31/4745 | (2006.01) | |
| A61K 39/00 | (2006.01) | |
| A61K 39/395 | (2006.01) | |
| A61K 47/34 | (2017.01) | |
| A61K 48/00 | (2006.01) | |
| A61L 27/26 | (2006.01) | |
| A61L 27/54 | (2006.01) | |
| A61L 27/58 | (2006.01) | |
| A61M 37/00 | (2006.01) | |

(52) U.S. Cl.
CPC .......... *A61K 9/0021* (2013.01); *A61K 9/5146* (2013.01); *A61K 31/437* (2013.01); *A61K 31/4745* (2013.01); *A61K 39/0005* (2013.01); *A61K 39/0011* (2013.01); *A61K 47/34* (2013.01); *A61K 2039/54* (2013.01); *A61K 2039/55511* (2013.01)

(58) Field of Classification Search
CPC ...... A61K 2039/54; A61K 2039/55511; A61K 31/437; A61K 31/4745; A61K 39/0005; A61K 39/0011; A61K 47/34; A61K 9/0021; A61K 9/5146
See application file for complete search history.

(56) References Cited

U.S. PATENT DOCUMENTS

| | | | |
|---|---|---|---|
| 8,414,871 B2 | 4/2013 | Kohn et al. | |
| 9,114,238 B2 | 8/2015 | Singh et al. | |
| 2013/0287832 A1 | 10/2013 | O'Hagan et al. | |

FOREIGN PATENT DOCUMENTS

| | | |
|---|---|---|
| KR | 10-2011-0022554 A | 3/2011 |
| KR | 10-2011-0065361 A | 6/2011 |
| KR | 10-2016-0124646 | 10/2016 |
| WO | WO 2008/130587 A2 | 10/2008 |

OTHER PUBLICATIONS

Basak, Rajib, and Ranjini Bandyopadhyay. "Encapsulation of hydrophobic drugs in Pluronic F127 micelles: effects of drug hydrophobicity, solution temperature, and pH." *Langmuir* 29.13 (Mar. 8, 2013): pp. 4350-4356.
Sahu, Abhishek, et al. "Encapsulation of curcumin in Pluronic block copolymer micelles for drug delivery applications." *Journal of biomaterials applications* 25.6 (2011): pp. 619-639.
Sharma, et al., "Self-assembly of PEO-PPO-PEO triblock copolymers in aqueous electrolyte solution." *Barc Newsletter* 285 (2007): pp. 84-87.
International Search Report for Corresponding International Application No. PCT/KR2017/002425 (2 Pages) (Jul. 10, 2017).

*Primary Examiner* — Jeffrey T. Palenik
(74) *Attorney, Agent, or Firm* — NSIP Law

(57) ABSTRACT

The method of manufacturing a self-assembled nanoparticle-releasing soluble microneedle structure comprises: dissolving a biocompatible amphiphilic block copolymer and a hydrophobic drug in a solvent to prepare a solution comprising a uniform mixture of the biocompatible amphiphilic block copolymer and the hydrophobic drug; removing the solvent from the solution to prepare a film comprising the uniform mixture; preparing an aqueous solution comprising an additive and a hydrophilic drug; adding the aqueous solution to the film and uniformly dispersing the film in the aqueous solution; injecting the aqueous solution into a template; and drying the template and separating the microneedle structure from the template.

6 Claims, 11 Drawing Sheets

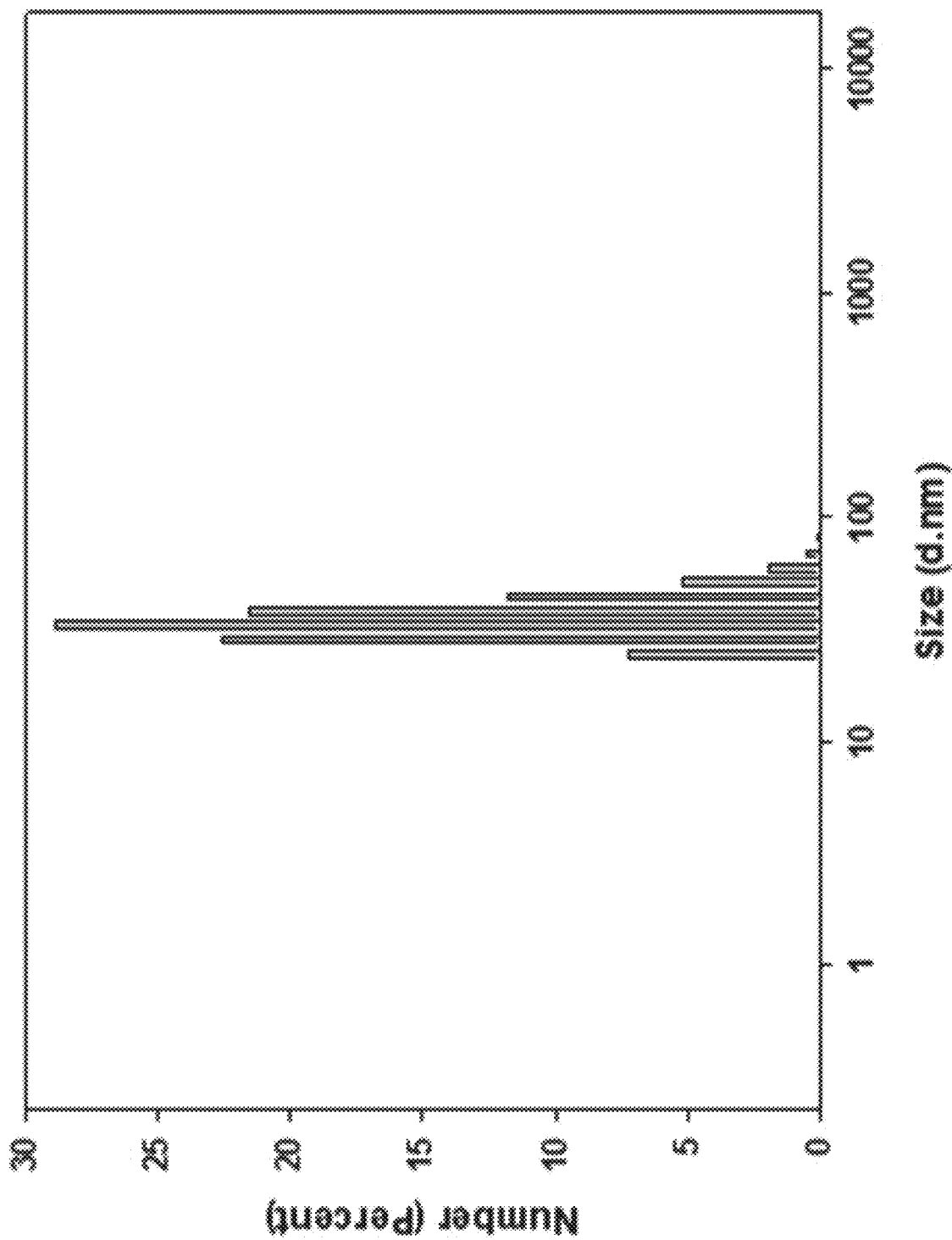

METHOD FOR PREPARING SELF-ASSEMBLED NANOPARTICLE RELEASING SOLUBLE MICRONEEDLE STRUCTURE

CROSS-REFERENCE TO RELATED APPLICATION

This application is a Divisional application of U.S. patent application Ser. No. 16/082,705 filed on Jan. 11, 2019, which is a U.S. National Stage Application of International Application No. PCT/KR2017/002425, filed on Mar. 7, 2017, which claims priority to and the benefit of Korean Patent Application Nos. 10-2016-0027240, filed on Mar. 7, 2016 and 10-2017-0027220, filed on Mar. 2, 2017, the disclosures of which are incorporated herein by reference in its entirety.

TECHNICAL FIELD

The present invention relates to a microneedle structure using a backbone material for a water-soluble structure capable of releasing drug-loaded self-assembled nanoparticles by dissolution, and a method of manufacturing the same.

BACKGROUND ART

Generally, one of the methods of delivering a drug, that is, a needle for direct hypodermic injection has disadvantages of pain and inflammation. In addition, bleeding may occur, and injection may be difficult according to age or a characteristic. Therefore, as an alternative thereto, microneedles have been actively studied because they can minimize pain, bleeding or inflammation, and enable local injection of a drug to be effectively and continuously input only to a site for injection.

Recently, attempts have been made to manufacture microneedles using a harmless biodegradable material. Particularly, there were increasing attempts to manufacture soluble microneedles using a polysaccharide or water-soluble polymer (for example, gelatin, hyaluronic acid or a mixture of hyaluronic acid/hydroxyprophile methylcellulose) (Korean Unexamined Patent Application Publication No. 10-2016-0124646)).

However, such water-soluble microneedles were i) very limited in loading of a hydrophobic drug due to the water-soluble property of a microneedle structure, and ii) exhibited toxicity in a corresponding site due to limited diffusion caused by precipitation in a site in which dermal administration occurred.

In addition, in the case of drug-coated needles, since a drug release is adjusted by rapid dissolution and simple diffusion, it is difficult to control a biological reaction, and when a needle structure is broken after use, the structure remains and thus has a risk of infection.

Meanwhile, for vaccine development, three kinds of technologies are largely needed: antigen, adjuvant, and vaccine delivery technologies. The antigen-related technology is associated with antigen design technology for inducing an immune response and mass production technology, the adjuvant technology is for maintaining an immune response at a sufficiently high level for a long time, and the vaccine delivery technology is used to determine an inoculation pathway of a vaccine.

Mostly, the inoculation of a vaccine is generally performed by subcutaneous, intradermal or intramuscular injection using a syringe, thereby decreasing the compliance of a patient, and the support of professional medical personnel is necessary.

Mainly, attenuated live vaccines or inactivated killed (inactivated) vaccines accounted for the largest part of early vaccines, but due to an increase in the requirement for stability, recently, a subunit vaccine clearly defined in structure and composition was mainly developed using genetic engineering technology. However, the subunit vaccine generally has lower immunogenicity than a conventional live vaccine or killed (inactivated) vaccine, and is used by mixing an adjuvant for increasing an immune response with a vaccine antigen. The adjuvant may increase the long-term immunogenicity of a vaccine, thereby reducing the number of inoculations, and increase immune responses in patients with a chronic disease or the elderly, which have reduced immunogenicity, thereby increasing a vaccination effect. While the most generally used adjuvant, an aluminum salt, is employed in most commercially available vaccines, it has been known that the adjuvant is not suitable for cancer vaccines necessary for a cell-mediated immune response because it generally serves to induce a Th2-type immune response, has excellent antigen-mediated immune response activity, but does not have a cell-mediated immune response.

Therefore, as a toll-like receptor (TRL) is a representative receptor that recognizes a bacterial cell wall, a lipopolysaccharide (LPS), and viral RNA/DNA, a TRL agonist has strong activity with respect to immune cells and highly reinforces an antibody-mediated immune response and a cell-mediated immune response, and thus has been widely developed as an adjuvant in recent years.

Numerous TRL agonist adjuvants have been developed in the form of an oil-in-water (O/W) emulsion or liposome due to low water solubility. While conventional water-soluble microneedles are suitable for vaccine antigen delivery, in the case of a hydrophobic adjuvant, it was difficult to manufacture a needle structure because of the water solubility of the structure, and also difficult to deliver a vaccine antigen to immune cells due to precipitation at an administration site after transdermal delivery.

Therefore, the inventors confirmed that a hydrophobic drug is transdermally delivered while contained in a microneedle structure without separate preparation using a biocompatible amphiphilic block copolymer having a property of dissolving in both an aqueous solution and an organic solvent, and then formation of hydrophobic drug-loaded nanoparticles can be induced through self-assembly of a structural polymer chain, and thus the present invention was completed.

DISCLOSURE

Technical Problems

The inventors had attempted to provide a microneedle structure for drug delivery, which can easily deliver a water- or fat-soluble drug, and thereby confirmed that an increase in solubility of aqueous drugs and activation of intracellular delivery can result from the formation of self-assembled nanoparticles when a hydrophobic drug is transdermally administered while contained in a microneedle structure without separate preparation using a biocompatible amphiphilic block copolymer having a property of dissolving in both an aqueous solution and an organic solvent, and therefore the present invention was completed.

Therefore, the present invention is directed to providing a self-assembled nanoparticle-releasing soluble microneedle structure consisting of a biocompatible amphiphilic block copolymer, which contains a water- or fat-soluble drug for easy delivery thereof.

The present invention is also directed to providing a method of manufacturing a self-assembled nanoparticle-releasing soluble microneedle structure consisting of a biocompatible amphiphilic block copolymer, which contains a water- or fat-soluble drug for easy delivery thereof.

However, technical problems to be solved in the present invention are not limited to the above-described problems, and other problems which are not described herein will be fully understood by those of ordinary skill in the art from the following descriptions.

Technical Solution

To attain the above-described objects, the present invention provides a self-assembled nanoparticle-releasing soluble microneedle structure consisting of a biocompatible amphiphilic block copolymer, which contains a water- or fat-soluble drug for easy delivery thereof.

In one exemplary embodiment of the present invention, the biocompatible amphiphilic block copolymer may be a di-block, tri-block or multi-block copolymer of a polymer in a hydrophilic domain and a polymer in a hydrophobic domain.

In another exemplary embodiment of the present invention, the polymer in a hydrophilic domain may be one or more selected from the group consisting of polyacrylic acid (PAA), polyethylene glycol (PEG), polyacrylonitrile (PAN), polyethylene oxide (PEO), polyvinyl acetate (PVAc), polyvinyl alcohol (PVA), and polymethylmethacrylate (PMMA).

In still another exemplary embodiment of the present invention, the polymer in a hydrophobic domain may be one or more selected from the group consisting of polypropylene oxide (PPO), polycaprolactone (PCL), polylactic acid (PLA), polyglycolic acid (PGA), poly(lactic-co-glycolic acid) (PLGA), polyanhydride, polyorthoester, polyester, polyesteramide, polystyrene, polydiene, polyisobutylene, polyisopropylacrylamide, polysiloxane, poly(2-vinyl naphthalene), poly(vinyl pyridine and N-methyl vinyl pyridinium iodide)), and poly(vinyl pyrrolidone).

In yet another exemplary embodiment of the present invention, the biocompatible amphiphilic block copolymer is preferably one or more selected from the group consisting of a poloxamer (polyethylene oxide-polypropylene oxide-polyethylene oxide) (PEO-PPO-PEO)) tri-block copolymer, a poloxamer (polypropylene oxide-polyethylene oxide-polypropylene oxide) (PPO-PEO-PPO)) tri-block copolymer, a polyethylene oxide-polylactic acid-polyethylene oxide (PEO-PLA-PEO) tri-block copolymer, a polylactic acid-polyethylene oxide-polylactic acid (PLA-PEO-PLA) tri-block copolymer, a polyethylene oxide-polyglycolic acid-polyethylene oxide (PEO-PGA-PEO) tri-block copolymer, a polyglycolic acid-polyethylene oxide-polyglycolic acid (PGA-PEO-PGA) tri-block copolymer, a polyethylene oxide-poly(lactic-co-glycolic acid)-polyethylene oxide (PEO-PLGA-PEO) tri-block copolymer, a poly(lactic-co-glycolic acid)-polyethylene oxide-poly(lactic-co-glycolic acid) (PLGA-PEO-PLGA) tri-block copolymer, a polyethylene oxide-polycaprolactone-polyethylene oxide (PEO-PCL-PEO) tri-block copolymer, a polycaprolactone-polyethylene oxide-polycaprolactone (PCL-PEO-PCL) tri-block copolymer, a polyethylene oxide-polylactic acid (PEO-PLA) di-block copolymer, a polyethylene oxide-polyglycolic acid (PEO-PGA) di-block copolymer, a polyethylene oxide-poly(lactic-co-glycolic acid) (PEO-PLGA) di-block copolymer, and a polyethylene oxide-polycaprolactone (PEO-PCL) di-block copolymer.

In yet another exemplary embodiment of the present invention, the biocompatible amphiphilic block copolymer is more preferably a poloxamer (polyethylene oxide-polypropylene oxide-polyethylene oxide) (PEO-PPO-PEO) tri-block copolymer.

In addition, the microneedle structure may contain a drug. There is no particular limitation to the contained drug, and either a water-soluble or fat-soluble drug may be used. Examples of available drugs may include one selected from the group consisting of a chemical substance, an adjuvant, a vaccine, a protein drug, a peptide drug, a nucleic acid molecule for gene therapy, an active material for a cosmetic, and an antibody for medical use, or a mixture of two or more thereof.

In one exemplary embodiment of the present invention, a content of the drug may be 0.0001 to 50 wt %, and preferably 0.01 to 20 wt % based on the total weight of the structure after drying. The content of the drug may be determined differently according to the minimal effective concentration of the drug and a type of the microneedle structure. The content is not limited to the above-mentioned range, and also includes the case containing a trace of the drug.

In another exemplary embodiment of the present invention, the structure may further include an additive which reinforces drug stability in the structure and needle strength. The additive may be one selected from the group consisting of hyaluronic acid, chitosan, polyvinyl alcohol, a carboxyvinyl polymer, an acrylvinyl polymer, dextran, carboxymethylcellulose, hydroxyethylcellulose, xanthan gum, locust bean gum, an ethylene-vinyl acetate polymer, cellulose acetate, acryl-substituted cellulose acetate, polyurethane, polycaprolactone, poly(lactic-co-glycolic acid) (PLGA), polylactic acid (PLA), polyglycolic acid (PGA), polyanhydride, polystyrene, polyvinyl acetate, polyvinyl chloride (PVC), polyvinyl fluoride (PVF), polyvinyl imidazole, a chlorosulfonate polyolefin, polyethylene oxide, polyvinylpyrrolidone (PVP), polyethylene glycol (PEG), polymethacrylate, hydroxypropylmethylcellulose (HPMC), ethylcellulose (EC), hydroxypropylcellulose (HPC), carboxymethylcellulose and cyclodextrin, or a mixture of two or more thereof.

In still another exemplary embodiment of the present invention, a composition ratio of the biocompatible amphiphilic block copolymer, the drug and the additive, which are included in the microneedle structure of the present invention, may vary according to a characteristic of the drug to be delivered or a type to be delivered.

In yet another exemplary embodiment of the present invention, the microneedle structure may be dissolved when inserted into the in vivo epithelium, thereby forming drug-loaded spherical self-assembled nanoparticles through self-assembly of a polymer chain.

In yet another exemplary embodiment of the present invention, the self-assembled nanoparticles may be spherical self-assembled nanoparticles, which have a micelle diameter of 10 to 2000 nm, and preferably 50 to 1000 nm.

In yet another exemplary embodiment of the present invention, the microneedle structure of the present invention may maintain a stable structure in an aqueous solution by forming self-assembled nanoparticles when dissolved in the aqueous solution, and easily deliver the loaded drug as well as increasing drug solubility in the aqueous solution during delivery of a hydrophobic drug, thereby facilitating hydrophobic drug delivery or simultaneous transdermal delivery of an antigen for a vaccine and a hydrophobic adjuvant.

In addition, the present invention provides a method of manufacturing a self-assembled nanoparticle-releasing soluble microneedle structure, which includes: the first operation of preparing a mixed solution by dissolving a biocompatible amphiphilic block copolymer and a drug in a solvent; and the second operation of manufacturing a microneedle structure using the mixed solution.

In one exemplary embodiment of the present invention, the solvent may be water, an organic solvent or a mixture thereof.

In another exemplary embodiment of the present invention, the organic solvent may be a volatile organic solvent, such as dichloromethane ($CH_2Cl_2$), tetrahydrofuran (THF), acetonitrile, ethyl acetate, acetone, ethanol, methanol or trifluoroalcohol (TFA), but the present invention is not necessarily limited thereto.

In still another exemplary embodiment of the present invention, a concentration of the biocompatible amphiphilic block copolymer in the mixed solution may be 5 to 50% (volume per volume; v/v).

In yet another exemplary embodiment of the present invention, the biocompatible amphiphilic block copolymer is as described above.

In yet another exemplary embodiment of the present invention, the microneedle structure of the present invention may be manufactured using the mixed solution, and as a manufacturing method, conventionally known methods can be used without limitation.

Preferably, the second operation may include: administering the mixed solution of the drug and the biocompatible amphiphilic block copolymer into a template, performing centrifugation under a vacuum and then injecting the resulting product into a cavity of the template; forming a microneedle structure by drying the template into which the mixed solution of the drug and the biocompatible amphiphilic block copolymer is injected; and separating the microneedle structure from the template.

In yet another exemplary embodiment of the present invention, the template may be an elastic mold such as polydimethylsiloxane (PDMS), which is prepared by known soft lithography. A technique for preparing a PDMS mold may be a type of plastic processing technology, and thus a desired molding structure may be obtained by various methods including casting, injection, hot-embossing, etc. In one example, a master mold may be prepared by coating a photosensitive material on a substrate such as a silicon wafer or glass and performing patterning using a photo mask, casting PDMS as a template, followed by sintering, resulting in a PDMS mold functioning as a stamp.

In yet another exemplary embodiment of the present invention, there is no particular limitation to the drug, and either a water-soluble or fat-soluble drug may be used. Examples of available drugs may include one selected from the group consisting of a chemical substance, an adjuvant, a vaccine, a protein drug, a peptide drug, a nucleic acid molecule for gene therapy, an active material for a cosmetic, and an antibody for medical use, or a mixture of two or more thereof.

In yet another exemplary embodiment of the present invention, the drug may be used at 0.0001 to 50 wt %, and preferably 0.01 to 20 wt % based on the total weight of the structure after drying. A content of the drug may be determined differently according to the minimal effective concentration of the drug and a type of the microneedle structure, and the content is not limited to the above-mentioned range, and also includes the case containing a trace of drug.

In yet another exemplary embodiment of the present invention, in terms of drug stability in the structure, the mixed solution in the first operation may be one selected from the group consisting of hyaluronic acid, chitosan, polyvinyl alcohol, a carboxyvinyl polymer, an acrylvinyl polymer, dextran, carboxymethylcellulose, hydroxyethylcellulose, xanthan gum, locust bean gum, an ethylene-vinyl acetate polymer, cellulose acetate, acryl-substituted cellulose acetate, polyurethane, polycaprolactone, poly(lactic-co-glycolic acid) (PLGA), polylactic acid (PLA), polyglycolic acid (PGA), polyanhydride, polystyrene, polyvinyl acetate, polyvinyl chloride (PVC), polyvinyl fluoride (PVF), polyvinyl imidazole, a chlorosulfonate polyolefin, polyethylene oxide, polyvinylpyrrolidone (PVP), polyethylene glycol (PEG), polymethacrylate, hydroxypropylmethylcellulose (HPMC), ethylcellulose (EC), hydroxypropylcellulose (HPC), carboxymethylcellulose and cyclodextrin, or a mixture of two or more thereof.

The drying method may be to perform heating to 4° C. to 500° C. under a vacuum according to the characteristics of a drug, a block copolymer and a solvent. The drying temperature may be adjusted according to the characteristics of a drug, a block copolymer and a solvent.

In addition, the present invention provides a method of preventing or treating a disease, which includes administering a self-assembled nanoparticle-releasing soluble microneedle structure into a subject.

In addition, the present invention provides a use of the self-assembled nanoparticle-releasing soluble microneedle structure for preventing or treating a disease.

Advantageous Effects

The present invention relates to a self-assembled nanoparticle-releasing soluble microneedle structure and a manufacturing method thereof, and the inventors had attempted to provide a microneedle structure for drug delivery, which can easily deliver a water-soluble or fat-soluble drug, and thereby confirmed that, when a hydrophobic drug was transdermally administered while contained in a microneedle structure without separate preparation using a biocompatible amphiphilic block copolymer having a property of dissolving in both an aqueous solution and an organic solvent, the formation of self-assembled nanoparticles results in an increase in drug solubility in an aqueous solution and activation of intracellular delivery, and thus the present invention was completed.

According to the present invention, an aqueous or hydrophobic drug can be delivered while loaded in microneedles, and particularly, a fat-soluble drug is delivered while loaded in micelle-type self-assembled nanoparticles formed by the dissolution of the structure. Accordingly, the solubility in an aqueous solution can be greatly increased, such that an existing drug with poor absorption is able to be delivered to the body through the skin, and thus it is expected to be useful for enhancing the efficiency of simultaneous delivery of a vaccine antigen and a hydrophobic vaccine adjuvant.

DESCRIPTION OF DRAWINGS

FIG. 1 shows the structure of a soluble microneedle manufactured in Example 1 below, wherein

FIG. 2 shows the formation of spherical self-assembled nanoparticles having a size of 33±8.73 nm by dissolving a soluble microneedle in an aqueous solution, wherein FIG. 2B is an SEM image.

FIG. 3 shows the release profiles of ovalbumin (OVA) and R848 from a soluble microneedle, wherein

FIG. 4 shows the intracellular delivery effect of nanoparticles formed by self-assembly after being released from microneedles, wherein

FIG. 7 shows the results of verifying the antitumor effect of OVA and R848-loaded soluble microneedles in mouse tumor models, wherein

MODES OF THE INVENTION

Figure 1A:
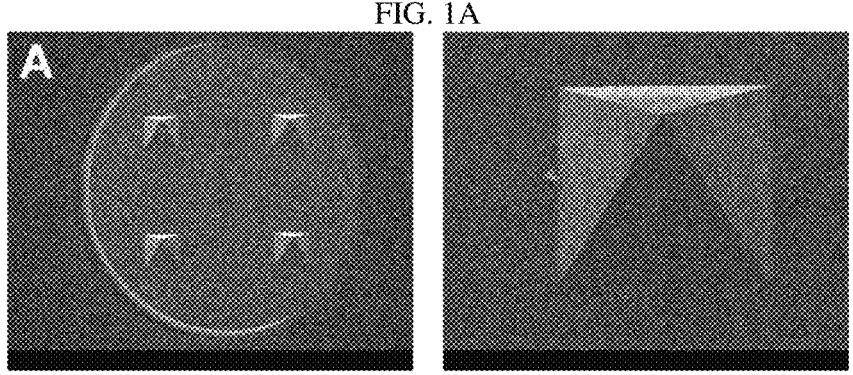
FIG. 1A is a scanning electron microscope (SEM) image.

The present invention relates to a self-assembled nanoparticle-releasing soluble microneedle structure and a preparation method thereof, and the inventors confirmed that, when a hydrophobic drug was loaded in a microneedle structure without separate preparation and transdermally administered using a biocompatible amphiphilic block copolymer having a property of dissolving in both an aqueous solution and an organic solvent, the formation of self-assembled nanoparticles result in an increase in drug solubility in an aqueous solution and activation of intracellular delivery, and thus the present invention was completed.

Therefore, the present invention is directed to providing a self-assembled nanoparticle-releasing soluble microneedle structure consisting of a biocompatible amphiphilic block copolymer which contains a water-soluble or fat-soluble drug for easy delivery thereof.

The present invention is also directed to providing a method of manufacturing a self-assembled nanoparticle-releasing soluble microneedle structure consisting of a biocompatible amphiphilic block copolymer which contains a water-soluble or fat-soluble drug for easy delivery thereof.

Hereinafter, the present invention will be described in detail.

In one exemplary embodiment of the present invention, microneedles are manufactured using PLURONIC™ F127 capable of forming spherical micelle-type self-assembled nanoparticles in an aqueous solution as an amphiphilic tri-block copolymer (see Example 1).

In another exemplary embodiment of the present invention, the microneedles manufactured by the method described in the exemplary embodiment are dissolved by floating on the water surface in a petri dish (Ø=30 mm) containing 500 µl distilled water, and the corresponding solution is taken and dried in a TEM grid (formvar coated), followed by confirming the formation of spherical particles (see Example 2).

In still another exemplary embodiment of the present invention, OVA and Resiquimod (R848) release profiles from soluble microneedles manufactured by the method described in the exemplary embodiment are identified (see Example 3).

In yet another exemplary embodiment of the present invention, soluble microneedles in which a hydrophobic fluorescent material DiD (Invitrogen, Carlsbad, CA, USA) used in cell membrane staining is loaded are manufactured according to the method described in the exemplary embodiment to confirm nanoparticles produced from the microneedles can mediate intracellular delivery of a hydrophobic material (drug) by cellular endocytosis (see Example 4).

In yet another exemplary embodiment of the present invention, when the soluble microneedles manufactured by the method described in the exemplary embodiment are administered to an animal epithelium, a delivery profile for a hydrophobic drug into the epithelium is identified (see Example 5).

In yet another exemplary embodiment of the present invention, OVA and Resiquimod (R848)-loaded soluble microneedles are manufactured according to the method described in the exemplary embodiment to confirm the production of total anti-OVA antibodies (see Example 6).

In yet another exemplary embodiment of the present invention, for a cancer immunotherapy model experiment, OVA and Resiquimod (R848)-loaded soluble microneedles are manufactured according to the method described in the exemplary embodiment, and then mice as experimental subjects are classified into groups according to an administered drug and an administration route and a therapeutic effect of a tumor vaccine is measured (see Example 7).

According to the above results, as a self-assembled nanoparticle-releasing soluble microneedle structure according to the present invention, the microneedle structure manufactured using the biocompatible amphiphilic block copolymer having a property of dissolving in both an aqueous solution and an organic solvent may be used for various objects and uses, for example, increasing simultaneous delivery efficiency of a vaccine, an antigen and a hydrophobic vaccine adjuvant.

Hereinafter, to help in understanding the present invention, exemplary examples will be suggested. However, the following examples are merely provided to more easily understand the present invention, and not to limit the present invention.

EXAMPLES

Example 1: Manufacture of Microneedles

After a tri-block copolymer, PLURONIC™ F127, was dissolved in ethanol to the final concentration of 15%, a solution in which a hydrophobic molecule was dissolved in ethanol (1,1'-dioctadecyl-3,3,3',3'-tetramethylindodicarbocyanine iodide (DiD) or Resiquimod (R848)) was uniformly mixed, and then an ethanol solvent present in the solution was removed using a rotary evaporator.

A film was obtained, the remaining solvent was completely removed by evaporation using nitrogen, a previously prepared aqueous solution containing polyethylene glycol (PEG MW 6000) and a hydrophilic molecule, OVA, was added to the film, and the film was uniformly dispersed in the aqueous solution using a sonicator, followed by filtering the aqueous solution to remove an undissolved material.

Soluble microneedles were manufactured by injecting 0.15 ml of the aqueous solution into a reusable negative-patterned template for a polydimethylsiloxane (PDMS) microneedle, which has a size of 1 cm×1 cm, at room temperature, performing centrifugation using a swing bucket rotor at 4° C. and 2,000 rpm for 10 minutes, and drying the resultant product in a vacuum trap-installed vacuum oven under a vacuum.

Figure 1B:
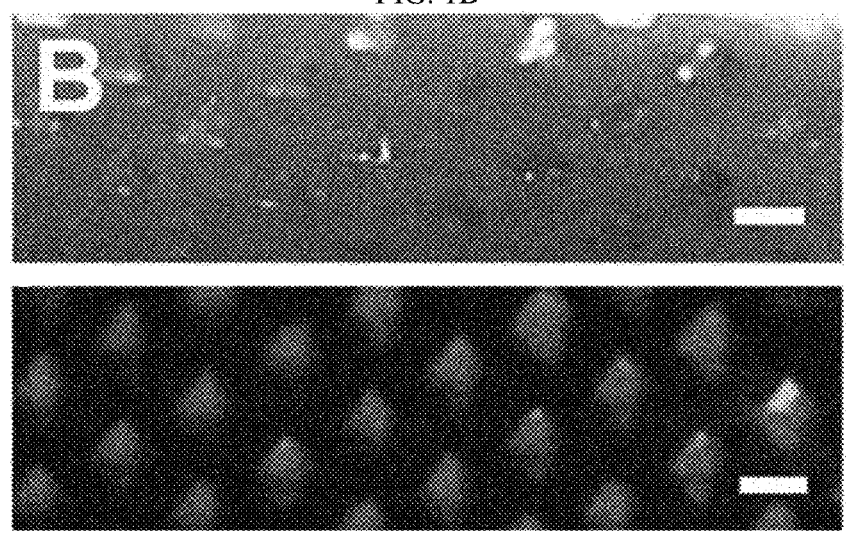
FIG. 1B is a set of a stereoscopic microscope image (top) and a fluorescence microscope image (bottom) of a microneedle in which a hydrophobic model drug, such as 1,1'-dioctadecyl-3,3,3',3'-tetramethylindodicarbocyanine, a 4-chlorobenzenesulfonate salt, (DiD) is loaded.
Figure 1C:
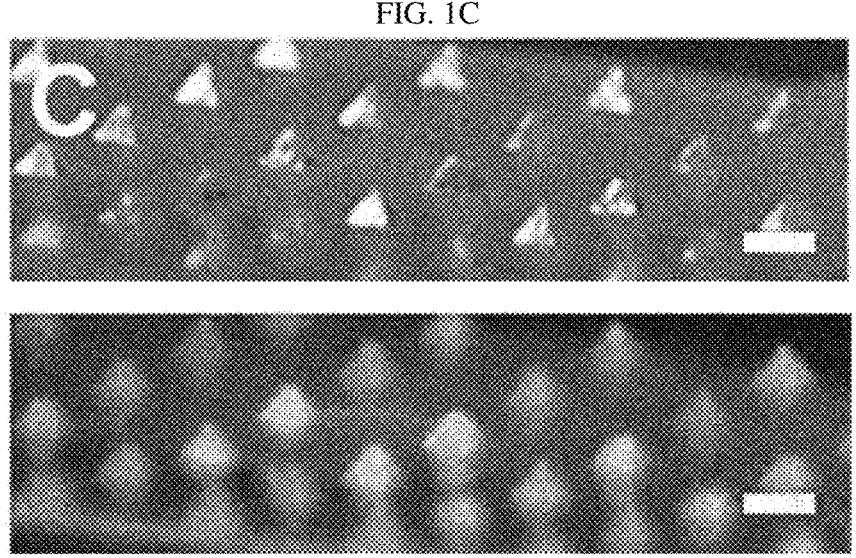
FIG. 1C is a set of a stereoscopic microscope image (top) and a fluorescence microscope image (bottom) of a microneedle in which a hydrophobic adjuvant, Resiquimod (R848) is loaded.

An adhesive tape with a size of 2 cm×2 cm was attached to and then detached from a base plate of the dried microneedles, thereby obtaining complete microneedles as shown in FIG. 1.

Example 2: Dissolution of Microneedles

Figure 2A:
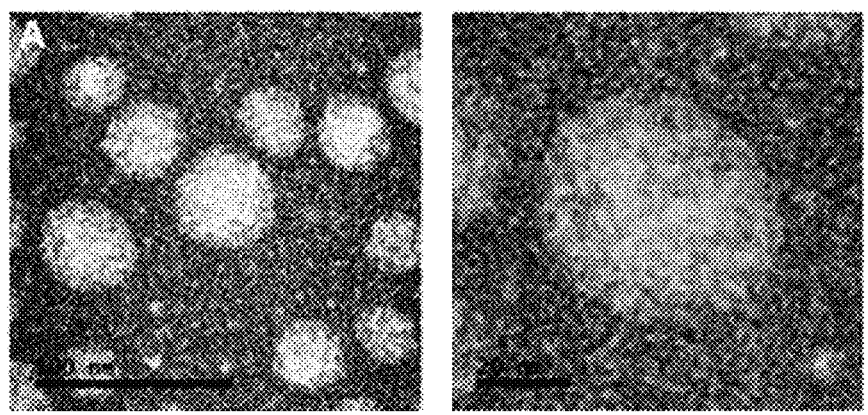
FIG. 2A shows the size distribution of particles analyzed by a light scattering method.

Spherical micelle-type self-assembled nanoparticles can be formed in an aqueous solution using the PLURONIC™ F127 used in Example 1 as an amphiphilic tri-block copolymer (see the description on the polymeric micelles of FIG. 2A).

A paraffin film (Parafilm®) was placed on a Styrofoam support, microneedles were applied and then pressed vertically, and then the film and the microneedles were separated from the Styrofoam support. Afterward, the film perforated by the microneedles and the microneedles were floated on the water surface in a Petri dish (Ø=30 mm) containing 500 μl of distilled water to dissolve the microneedles, and 30 minutes later, the corresponding solution was taken and then dried on a TEM grid (formvar coated). As a result, as shown in FIG. 2A, formation of spherical particles could be confirmed using a transmission electron microscope.

In addition, as shown in FIG. 2B, it was observed that the size of a micelle in the solution analyzed by light scattering is 33±8.73 nm.

Example 3: Release Profiles for OVA and Resiquimod (R848)

To observe the profiles of releasing OVA and Resiquimod (R848) from the soluble microneedles manufactured by the method of Example 1, the soluble microneedles were put into phosphate buffered saline (PBS, pH 7.4), stored at 37° C., and then a sample was obtained at predetermined intervals (0, 1, 2, 3, 4, 5, 10, 20, 30, 60, and 90 minutes), followed by replacement with the same volume of a new release solution.

Figure 3A:
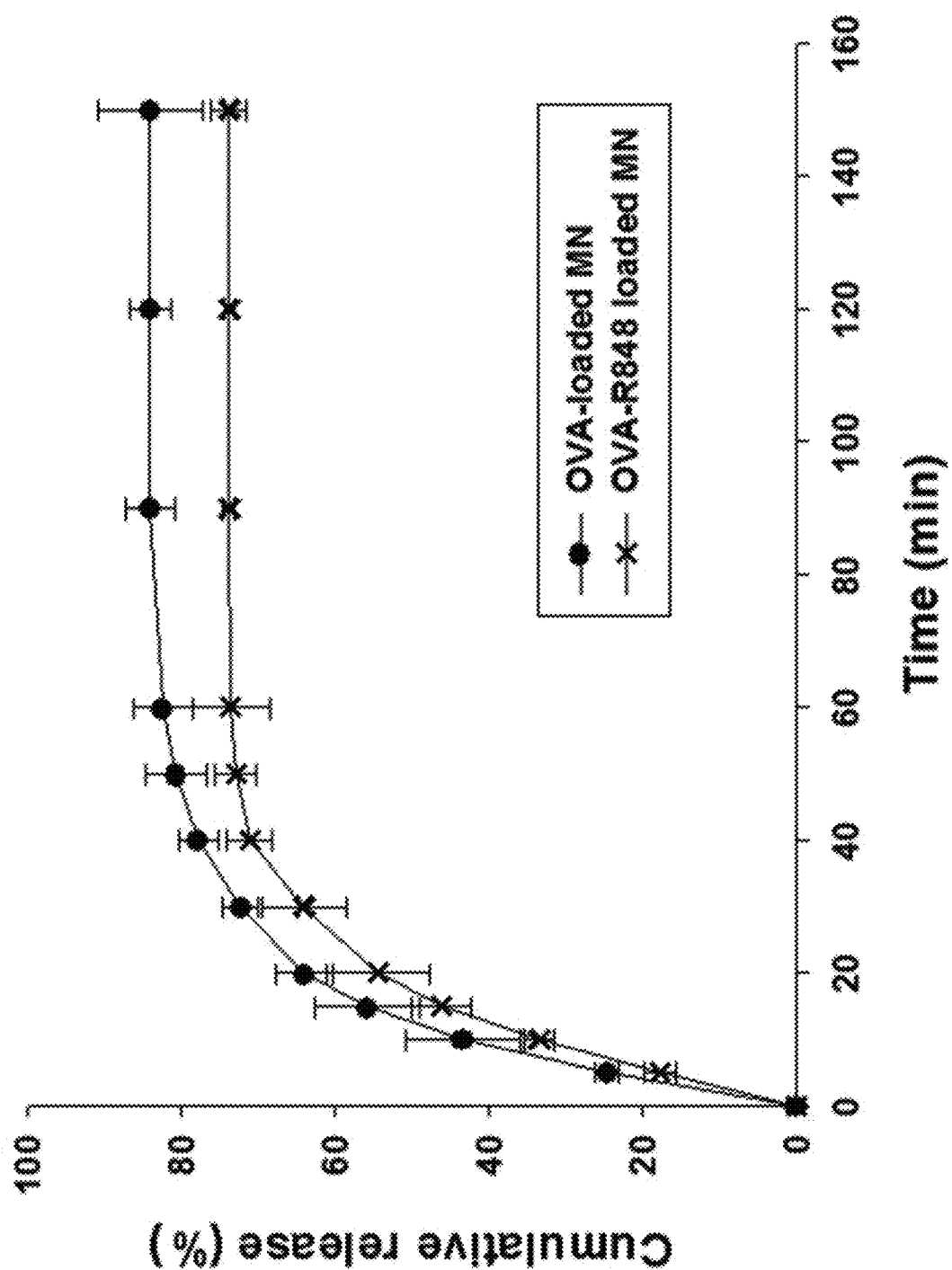
FIG. 3A shows the OVA release profile in an OVA only-containing microneedle (OVA-loaded MN) and an OVA/R848-containing microneedle (OVA-R848-loaded MN)

As a result, as shown in FIG. 3A, an OVA release profile from each of OVA only-containing microneedles (OVA-loaded MN) and OVA/R848-containing microneedles (OVA-R848 loaded MN) was able to be identified by the bicinchoninic acid (BCA) assay (micro plate reader, Multiskan GO, Thermo Fisher Scientific, Vantaa, Finland) at 590 nm.

Figure 3B:
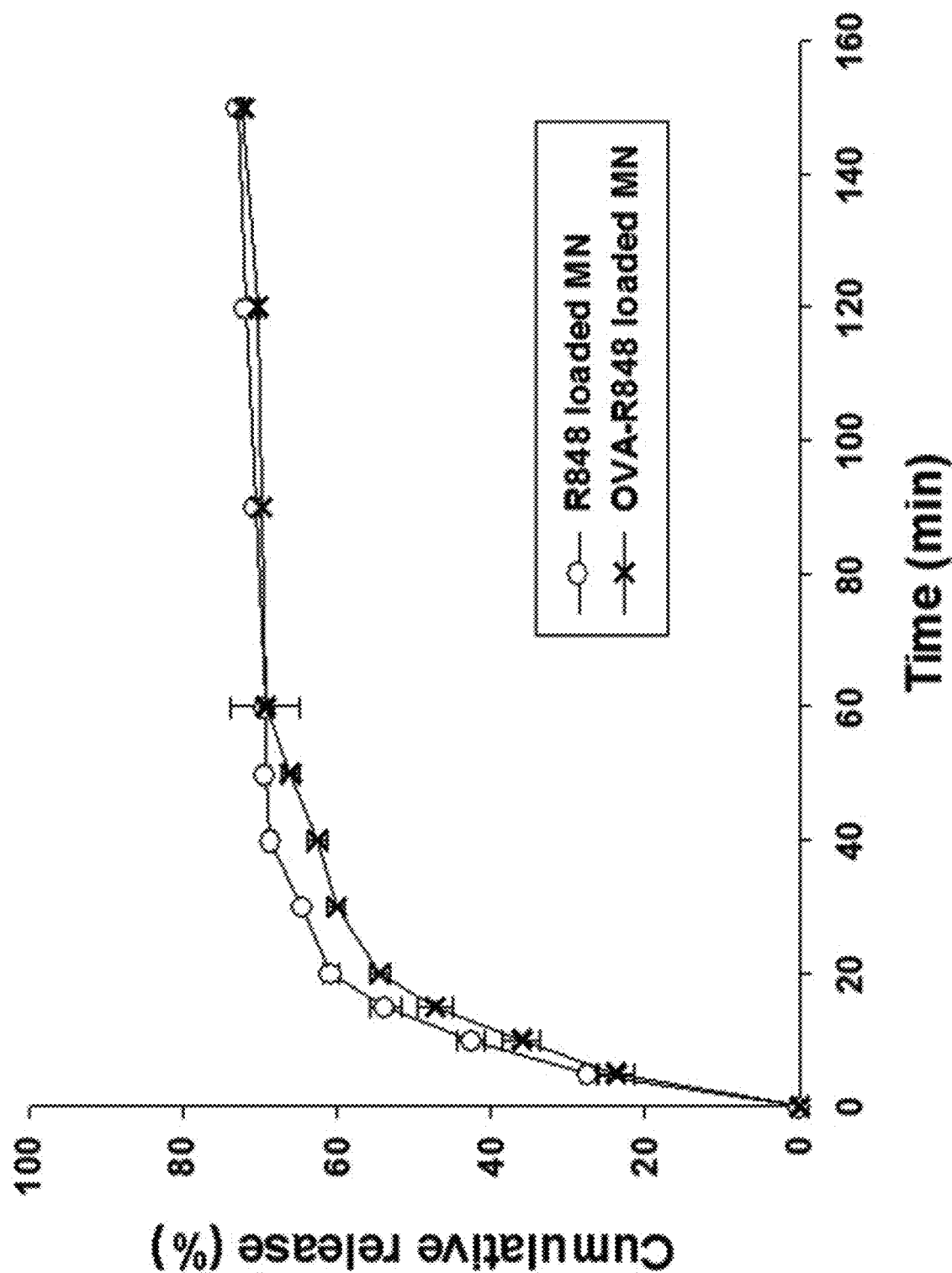
FIG. 3B shows the R848 release profile in a R848 only-containing microneedle (R848-loaded MN) and an OVA/R848 contained microneedle (OVA-R848 loaded MN).

In addition, the absorbance with respect to R848 was calculated and quantified at 327 nm using a UV-Vis scanner (TECAN Infinite M500 microplate reader), confirming that, as shown in FIG. 3B, an R848 release profile from each of R848 only-containing microneedles (R848-loaded MN) and OVA/R848-containing microneedles (OVA-R848 loaded MN).

Example 4: Intracellular Delivery of Nanoparticles Produced from Soluble Microneedles Since nanoparticles can be delivered into the cytosol by the endocytosis mechanism of cells, the intracellular delivery of the nanoparticles produced by the method of Example 2 was observed.

To this end, soluble microneedles in which a hydrophobic fluorescent material, DiD (Invitrogen, Carlsbad, CA, USA), used in cell membrane staining, was loaded were manufactured according to the method described in Example 1. Afterward, cells (HCT-116) were treated with a solution in which the microneedles were dissolved according to the method of Example 2, 4 hours later, intracellular delivery of nanoparticles produced from the soluble microneedles was observed using a confocal fluorescence microscope.

Figure 4A:
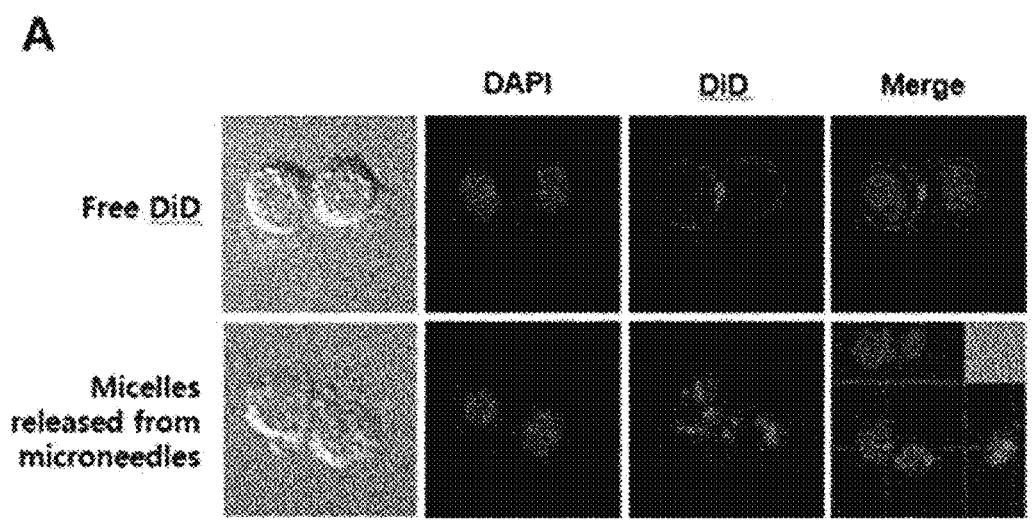
FIG. 4A shows a confocal fluorescence microscope image.
Figure 4B:
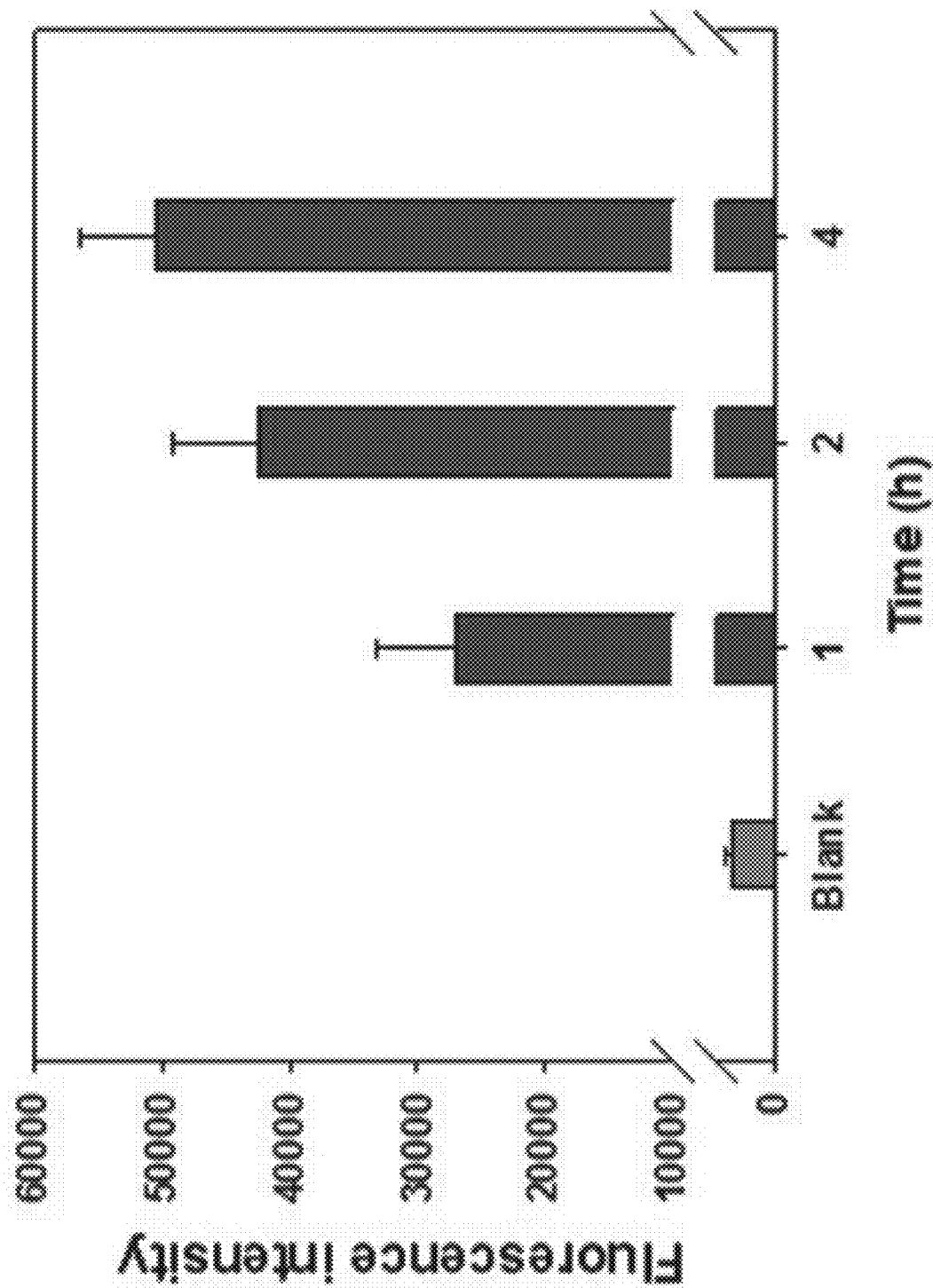
FIG. 4B shows the result of observing the intracellular delivery effect of a fluorescent material over time (incubation time).

As a result, as shown in FIG. 4A, it was confirmed that DiD dissolved in dimethyl sulfoxide (DMSO) stained the cell membrane, whereas micelle nanoparticles produced from the microneedles can be delivered into the cytosol, and as shown in FIG. 4B, the intracellular delivery effect of a fluorescent material according to time (incubation time) was also confirmed.

According to the results, it can be seen that the nanoparticles produced from the microneedles can mediate the intracellular delivery of a hydrophobic material (drug) by cellular endocytosis.

Example 5: Experiment for Animal Epithelial Injection of Soluble Microneedles To observe an intra-epithelial delivery profile for a hydrophobic drug after microneedles were applied to an animal epithelium, soluble microneedles in which a hydrophobic fluorescent material DiD (Invitrogen, Carlsbad, CA, USA), which is used in cell membrane staining, and a fluorescent material (FITC)-conjugated hydrophilic material FITC-OVA, were loaded were manufactured according to the method of Example 1.

The microneedles were applied and fixed to the epithelium of a mouse, and 30 minutes later, fluorescence distribution over time was observed using in situ optical imaging equipment (Optix MX3).

Figure 5A:
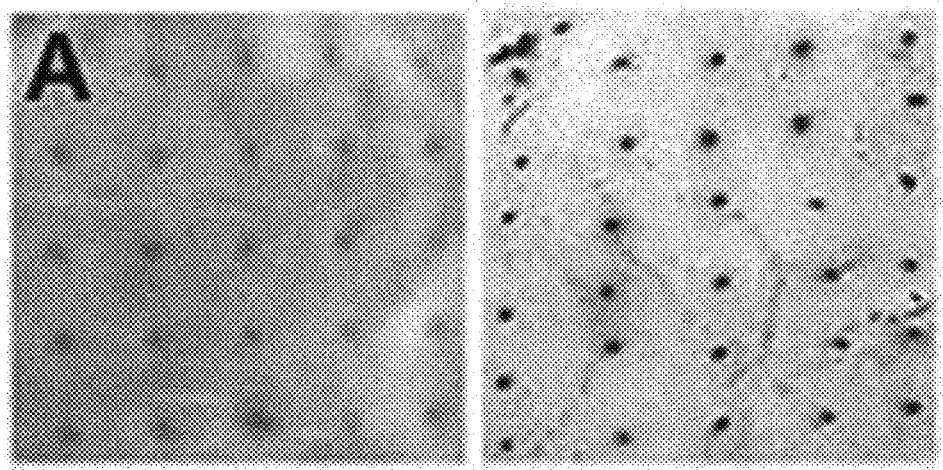
FIG. 5A shows the dermal structure after microneedles are applied to a peeled murine epithelium (optical microscope and SEM images)
Figure 5B:
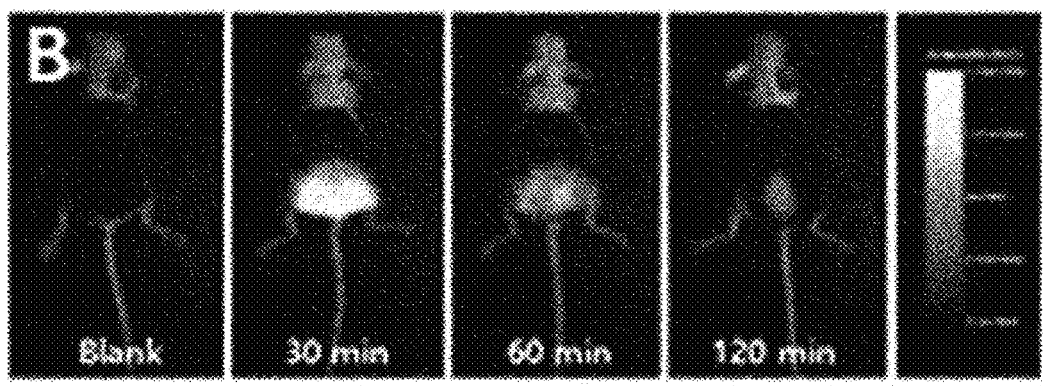
FIGS. 5B and 5C show DiD fluorescence over time (FIG. 5B) and the intraepithelial distribution and loss of FITC-OVA (FIG. 5C) using in vivo optical imaging equipment after soluble microneedles in which a hydrophobic fluorescent material (DiD) and fluorescein isothiocyanate (FITC)-labeled hydrophilic OVA are loaded are applied to a mouse epithelium for 30 minutes.
Figure 5C:
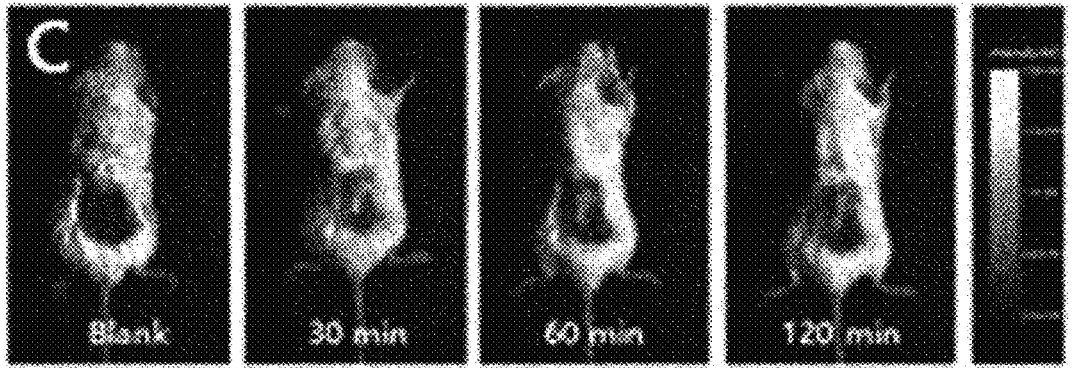

As a result, as shown in FIG. 5, the microneedles can successfully pass through the epithelium of a mouse (FIG. 5A), and can release a hydrophobic drug (DiD; see FIG. 5B) and a hydrophilic drug (OVA; FIG. 5C) into the epithelium by decomposing the microneedles within 30 minutes after direct application of the microneedles to the mouse epithelium, thus reaching inside the epithelium.

Example 6: Production of Anti-OVA-Specific Immunoglobulin from Soluble Microneedles Containing Hydrophilic OVA and Hydrophobic R848

Production of total anti-OVA antibodies was evaluated using enzyme-linked immunosorbent assay (ELISA).

To this end, OVA and Resiquimod (R848)-soluble microneedles were manufactured according to the method of Example 1.

For transdermal delivery of an antigen (OVA), 7 days after the third inoculation to a microneedle-applied mouse group, a blood sample was obtained, and inoculation was performed once a week. To confirm the difference in antibody production over time, 1, 2 and 4 weeks after the final injection, a serum sample was collected, the formulation of an OVA-specific immunoglobulin was observed using ELISA.

Figure 6:
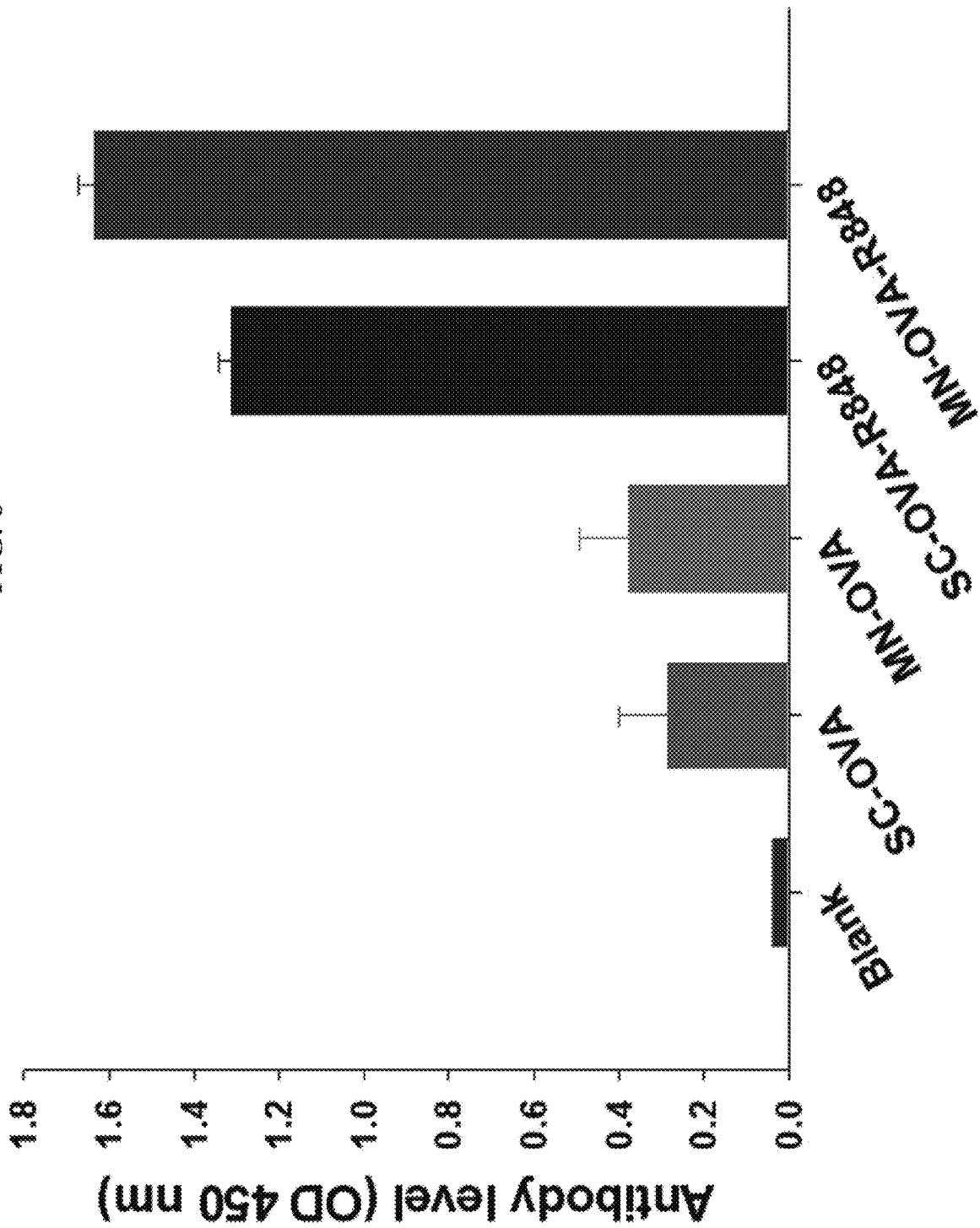
FIG. 6 shows the effect of the use of soluble microneedles (MN) and the antibody formation of an adjuvant (R848) for production of an OVA-specific immunoglobulin (subcutaneous injection using hypodermic syringe; SC).

Consequently, as shown in FIG. 6, it was confirmed that, in inoculation of an adjuvant (R848)-loaded microneedle, a more excellent antibody-forming effect was exhibited.

Example 7: Anti-Tumor Immunotherapeutic Effect of OVA and R848-Loaded Microneedles For a cancer immunotherapy model experiment, OVA and Resiquimod (R848)-loaded soluble microneedles were manufactured according to the method of Example 1.

For this experiment, an experiment was performed by classifying mice into a PBS-treated group (Blank), a group in which 100 μg of OVA was delivered through two kinds of administration routes (subcutaneous injection (SC) using a hypodermic needle and microneedle (MN) injection), and a group in which both 100 μg of OVA and 50 μg of R848 are delivered through two types of administration routes (SC using a hypodermic needle and MN injection).

To measure a therapeutic effect of a tumor vaccine, E.G7-OVA cells were subcutaneously injected into the right part of C57BL/6 mouse dorsal tissue at a density of $1\times10^6$, and when a tumor volume reached approximately 100 mm$^3$, each preparation was administered regularly (2, 4, 6, 8, 12 and 14 days) to accomplish treatment. A tumor size was measured using a vernier caliper, and a tumor volume (V) was measured using the equation V=0.5×W 2×L. Here, W and L respectively refer to the minor axis and major axis of the tumor.

Figure 7A:
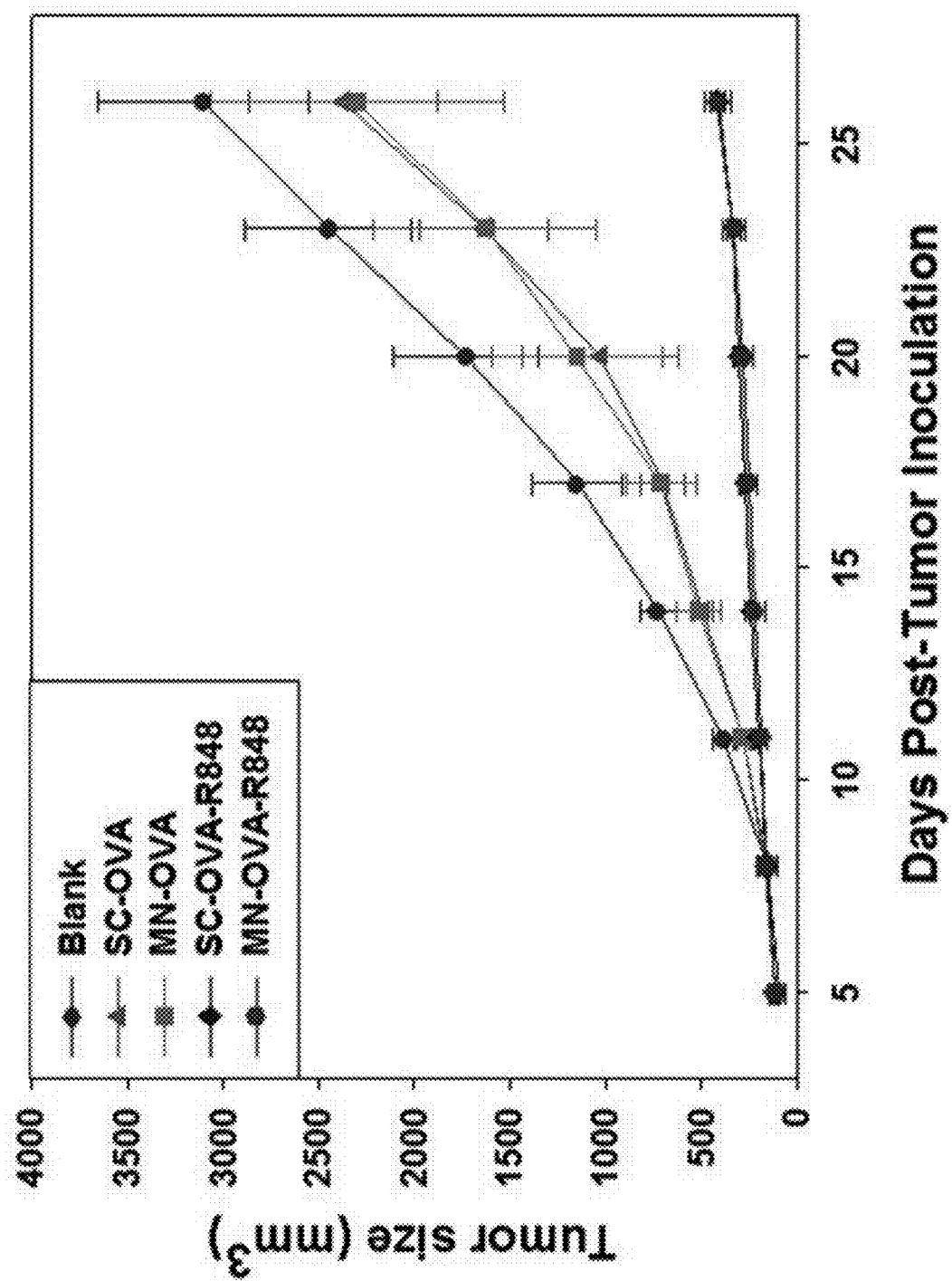
FIG. 7A shows a change in tumor size in OVA antigen-labeled E.G7-OVA cell xenograft mice.
Figure 7B:
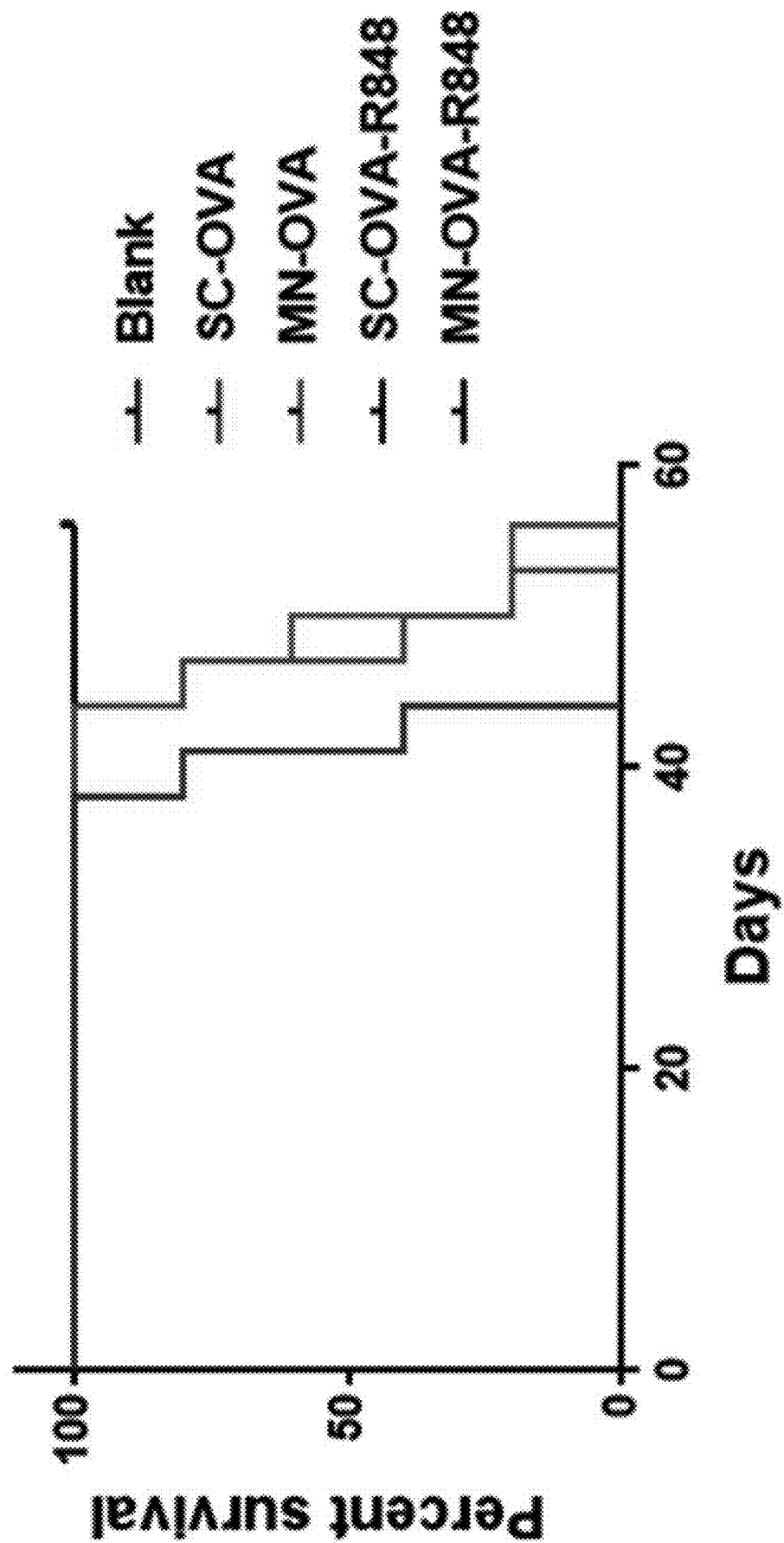
FIG. 7B shows the survival curve of tumor xenograft mice according to the antitumor effect of a preparation.

As shown in FIG. 7, a change in tumor size in an OVA antigen-labeled E.G7-OVA cell xenograft mouse was observed, and a volume of the solid tumor and a body weight of the mouse were measured every three days and recorded (see FIG. 7A). The survival curve (Kaplan-Meier curve) of the tumor xenograft mouse according to an antitumor effect of the preparation was calculated using a Graph Pad Prism program (see FIG. 7B).

Consequently, it can be seen that OVA and R848-loaded soluble microneedles exhibited an excellent tumor growth inhibitory effect, and all mice to which the OVA and R848-loaded microneedle preparation was applied survived for 60 days.

INDUSTRIAL APPLICABILITY

The present invention relates to a self-assembled nanoparticle-releasing soluble microneedle structure and a manufacturing method thereof, and according to the present invention, since a water-soluble or hydrophobic drug can be delivered while contained in microneedles, an existing drug having poor absorption can be delivered into a body through the skin. Therefore, it is expected that the microneedle structure of the present invention can be effectively used to improve the efficiency of performing simultaneous delivery of a vaccine antibody and a hydrophobic vaccine adjuvant in the future.

The invention claimed is:

1. A method of manufacturing a self-assembled nanoparticle-releasing soluble microneedle structure, comprising:
    dissolving a biocompatible amphiphilic block copolymer and a hydrophobic drug in a solvent to prepare a solution comprising a uniform mixture of the biocompatible amphiphilic block copolymer and the hydrophobic drug;
    removing the solvent from the solution to prepare a film comprising the uniform mixture;
    preparing an aqueous solution comprising an additive and a hydrophilic drug;
    adding the aqueous solution to the film and uniformly dispersing the film in the aqueous solution;
    injecting the aqueous solution into a template; and
    drying the template and separating the microneedle structure from the template.

2. The method of manufacturing a self-assembled nanoparticle-releasing soluble microneedle structure according to claim 1, wherein the solvent is water, dichloromethane (CH$_2$Cl$_2$), tetrahydrofuran, acetonitrile, ethyl acetate, acetone, ethanol, methanol, trifluoroalcohol or a mixture thereof.

3. The method of manufacturing a self-assembled nanoparticle-releasing soluble microneedle structure according to claim 1, wherein a concentration of the biocompatible amphiphilic block copolymer in the mixed solution is 5 to 50% (v/v).

4. The method of manufacturing a self-assembled nanoparticle-releasing soluble microneedle structure according to claim 1, wherein the biocompatible amphiphilic block copolymer is one or more selected from the group consisting of a polyethylene oxide-polypropylene oxide-polyethylene oxide tri-block copolymer, a polypropylene oxide-polyethylene oxide-polypropylene oxide tri-block copolymer, a polyethylene oxide-polylactic acid-polyethylene oxide tri-block copolymer, a polylactic acid-polyethylene oxide-polylactic acid tri-block copolymer, a polyethylene oxide-polyglycolic acid-polyethylene oxide tri-block copolymer, a polyglycolic acid-polyethylene oxide-polyglycolic acid tri-block copolymer, a polyethylene oxide-poly(lactic-co-glycolic acid)-polyethylene oxide tri-block copolymer, a poly(lactic-co-glycolic acid)-polyethylene oxide-poly(lactic-co-glycolic acid) tri-block copolymer, a polyethylene oxide-polycaprolactone-polyethylene oxide tri-block copolymer, a polycaprolactone-polyethylene oxide-polycaprolactone tri-block copolymer, a polyethylene oxide-polylactic acid di-block copolymer, a polyethylene oxide-polyglycolic acid di-block copolymer, a polyethylene oxide-poly(lactic-co-glycolic acid) di-block copolymer, and a polyethylene oxide-polycaprolactone di-block copolymer.

5. The method of manufacturing a self-assembled nanoparticle-releasing soluble microneedle structure according to claim 1, wherein the biocompatible amphiphilic block copolymer is a polyethylene oxide-polypropylene oxide-polyethylene oxide tri-block copolymer.

6. The method of manufacturing a self-assembled nanoparticle-releasing soluble microneedle structure according to claim 1, wherein the additive is hyaluronic acid, chitosan, polyvinyl alcohol, a carboxyvinyl polymer, an acrylvinyl polymer, dextran, carboxymethylcellulose, hydroxyethylcellulose, xanthan gum, locust bean gum, an ethylene-vinyl acetate polymer, cellulose acetate, acryl-substituted cellulose acetate, polyurethane, polycaprolactone, poly(lactic-co-glycolic acid), polylactic acid, polyglycolic acid, polyanhydride, polystyrene, polyvinyl acetate, polyvinyl chloride, polyvinyl fluoride, polyvinyl imidazole, a chlorosulfonate polyolefin, polyethylene oxide, polyvinylpyrrolidone, polyethylene glycol, polymethacrylate, hydroxypropylmethylcellulose, ethylcellulose, hydroxypropylcellulose, carboxymethylcellulose and cyclodextrin, or a mixture of two or more thereof.

* * * * *